United States Patent
Sugiyama et al.

(10) Patent No.: US 6,713,633 B1
(45) Date of Patent: Mar. 30, 2004

(54) COMPOUNDS CAPABLE OF CLEAVING DOUBLE-STRANDED DNA AND METHOD OF UTILIZATION OF THE SAME

(75) Inventors: Hiroshi Sugiyama, Tokyo (JP); Zhi-Fu Tao, Charlottesville, VA (US); Isao Saito, Kyoto (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/701,264

(22) PCT Filed: Mar. 10, 2000

(86) PCT No.: PCT/JP00/01461

§ 371 (c)(1),
(2), (4) Date: Aug. 8, 2001

(87) PCT Pub. No.: WO00/58312

PCT Pub. Date: Oct. 5, 2000

(30) Foreign Application Priority Data

Mar. 26, 1999 (JP) ............................................. 11-083591

(51) Int. Cl.[7] ......................................... A61K 31/4164
(52) U.S. Cl. ....................... 548/416; 514/387; 548/400; 548/422; 562/553
(58) Field of Search .................. 514/387, 19; 548/400, 548/422, 416; 562/553

(56) References Cited

U.S. PATENT DOCUMENTS 5,998,140 A * 12/1999 Dervan et al. ................. 435/6

FOREIGN PATENT DOCUMENTS

WO    WO 97/32850    9/1997

OTHER PUBLICATIONS

Z. Tao et al., *Angew. Chem. Int. Ed.*, 38(5):650–653 (1999).

H. Sugiyama et al., *Proc. Natl. Acad. Sci. USA*, 93:14405–14410 (1996).

* cited by examiner

*Primary Examiner*—Christopher S. F. Low
*Assistant Examiner*—David Lukton
(74) *Attorney, Agent, or Firm*—Peter F. Corless; Christine C. O'Day; Edwards & Angell, LLP

(57) ABSTRACT

Novel chemical species capable of simultaneously alkylating double-stranded DNA and cleaving the same; methods for alkylating and cleaving DNA by using these species; and anticancer agents with the use of these compounds. Compounds represented by the following general formula (I) which are capable of simultaneously alkylating double-stranded DNA and cleaving the same; a method for alkylating DNA and a method for cleaving double stranded DNA by using these compounds; and medicinal compositions with the use of these compounds: B—L—A(I) wherein B represents a chemical structure capable of recognizing the base sequence of DNA, for example, optionally substituted pyrrole-imidazole polyamide; A represents a chemical structure capable of binding to one base of DNA, for example, the alkylation moiety of duocarmycin A; and L represents a linker capable of binding the chemical structures A and B, for example, vinyl.

6 Claims, 3 Drawing Sheets

Fig. 2

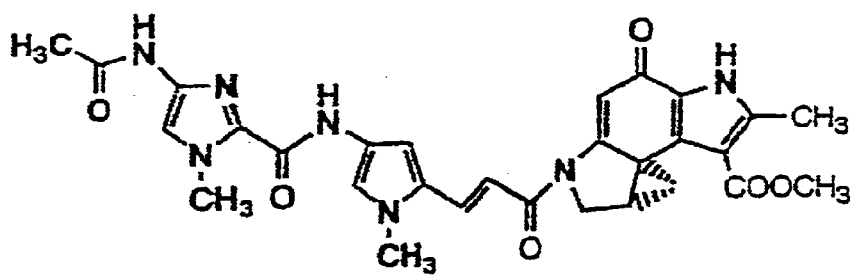

```
5'*- AGAATCAGGG GATAACGCAG GAAAGAACAT GTGAGCAAAA GGCCAGCAAA
3'- TCTTAGTCCC CTATTGCGTC CTTTCTTGTA CACTCGTTTT CCGGTCGTTT

AGGCCAGGAA CCGTAAAAAG GCCGCGTTGC TGGCGTTTTT CCATAGGCTC
    TCCGGTCCTT GGCATTTTTC CGGCGCAACG ACCGCAAAAA GGTATCCGAG
              Site 1            Site 2
    CGCCCCCCTG ACGAGCATCA CAAAAATCGA CGCTCAAGTC AGAGGTGGCG
    GCGGGGGGAC TGCTCGTAGT GTTTTTAGCT GCGAGTTCAG TCTCCACCGC AAACCCGACA GGACTATAAA GATACCAGGC GTTTCCCCCT GGAAGCTCCC
    TTTGGGCTGT CCTGATATTT CTATGGTCCG CAAAGGGGA  CCTTCGAGGG TCGTGCGCTC TCCTGTTCCG ACCCTGCCGC TTACCGGATA CCTGTCCGCC
    AGCACGCGAG AGGACAAGGC TGGGACGGCG AATGGCCTAT GGACAGGCGG TTTCTCCCTT CGGGAAGCGT GGCGCTTTCT CAATGCTCAC GCTGTAGGTA
    AAAGAGGGAA GCCCTTAGCA CCGCGAAAGA GTTACGAGTG CGACATCCAT TCTCAGTTCG GTGTAGGTCG TTCGCTCCAA GCTGGGCTGT GTGCACGAAC
    AGACTCAAGC CACATCCAGC AAGCGAGGTT CGACCCGACA CACGTGCTTG CCCCCGTTCA GCCCGACCGC TGCGCCTTAT CCGGTAACTA TCGTCTTGAG
    GGGGGCAAGT CGGGCTGGCG ACGCGGAATA GGCCATTGAT AGCAGAACTC TCCAACCCGG TAAGACACGA CTTATCGCCA CTGGCAGCAG CCACTGGTAA-3'
    AGGTTGGGCC ATTCTGTGCT GAATAGCGGT GACCGTCGTC GGTGACCATT-5'*
```

Fig. 3
Site 1
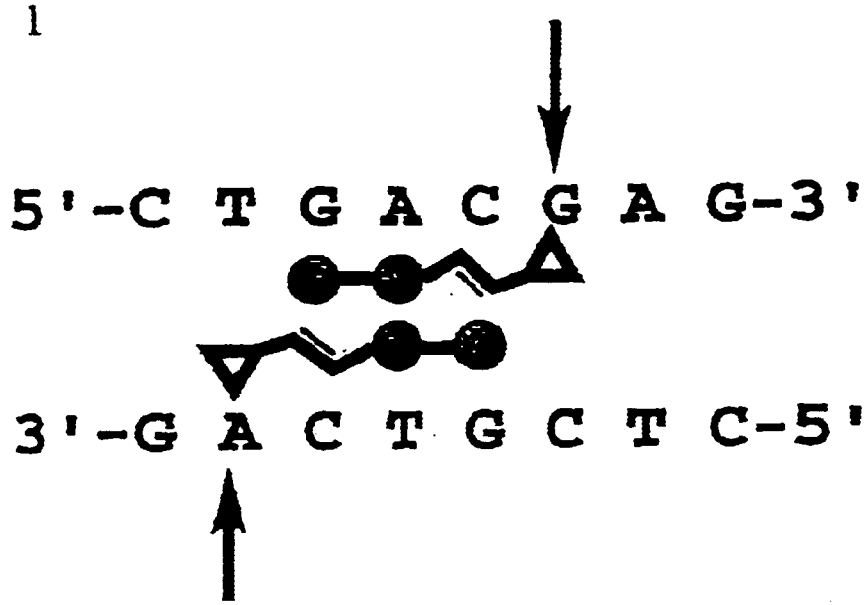
Site 2
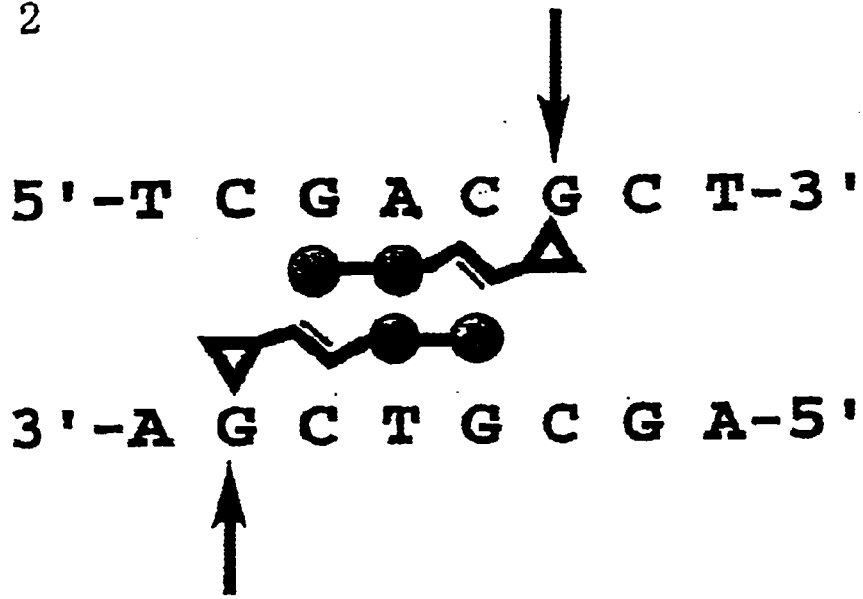

COMPOUNDS CAPABLE OF CLEAVING DOUBLE-STRANDED DNA AND METHOD OF UTILIZATION OF THE SAME

TECHNICAL FIELD

The present invention relates to a compound, which can be produced by chemical synthesis and can simultaneously alkylating and cleaving a double-strand DNA, a method for alkylating DNA using compound thereof, a method for cleaving double-strand DNA, and a pharmaceutical composition using compound thereof.

BACKGROUND ART

Base sequence of total gene, our human "blue print of life" is under elucidation by the human genome project without few years. The fact that the disease or the aging will occur, if this blue print is damaged or acquires the damage, is well known. As a result of progress in the human genome project, many diseases including cancer can be understood in the DNA level and the total medical science including diagnosis and prophylaxis may be changed revolutionarily. Further, a therapeutic method based on understanding in the DNA level of these diseases, namely development of pharmaceutical products targeting causal gene of disease and its product is highly expected, however mediatory studies for applying the fundamental studies to the clinical studies have only been just started. Anticancer agents used at present are antibiotics mainly selected by screening, and are originally not produced by microorganisms for the purpose of their cytotoxic action for cancer cells, and among them, almost no substances based on molecular biological knowledge of cancer are known. If expression of the intracellular specific gene can be freely controlled extracellularly, ultimate therapeutic method in the gene level can be achieved.

Recently, we have found that antibiotic duocarmycin constructed heterodimer with a molecule of the other species such as distamycin to achieve cooperatively molecular recognition of DNA, and effective alkylation of base sequence can be achieved as compared with the case of duocarmycin alone (Proc. Natl. Acad. Sci. USA 93, 14405, 1996). Based on the result of the discovery, pyrrole-imidazole polyamide is bound with the alkylation site of duocarmycin as a DNA recognition site and we have successfully synthesized the molecule which can selectively alkylating DNA at any base sequences (Japanese Patent Application No. Hei 10-260710). However, the compounds only binding with pyrrole-imidazole polyamide as the DNA recognition site in the alkylating moiety of duocarmycin can not only have insufficient alkylation activity but also alkylate only one strand base sequence.

We have examined alkylation reaction with these molecules and DNA using computer modeling such as molecular dynamics of these compounds in detail, and found that as a result of the insertion of the linker such as vinyl group into the location of the cylcopropane moiety (segment A), which was a reactive site of duocarmycin, an improved alkylation efficacy of DNA could be expected.

DISCLOSURE OF INVENTION

The present invention provides alkylating agent with improved efficiency of DNA alkylation. Further, we have found in the present study that the alkylating agent of the present invention showed dimer-like behavior as well as simultaneously alkylating and cleaving the double-strand DNA, and had an action as the artificial restriction enzyme for the specific base sequence.

Consequently, the present invention provides novel chemical species, which can simultaneously alkylating and cleaving the double-strand DNA. Further, the present invention provides a method for alkylating and cleaving DNA using chemical species thereof.

The present invention further provides anticancer agent using compound thereof.

BRIEF DESCRIPTION OF DRAWING

FIG. 2 shows base sequence of DNA and a chemical structure of ImPyLDu86 used in the experiment.

FIG. 3 is a schematic representation of cleavage site of DNA by a compound of the present invention.

BEST MODE FOR CARRYING OUT THE INVENTION

Figure 1:
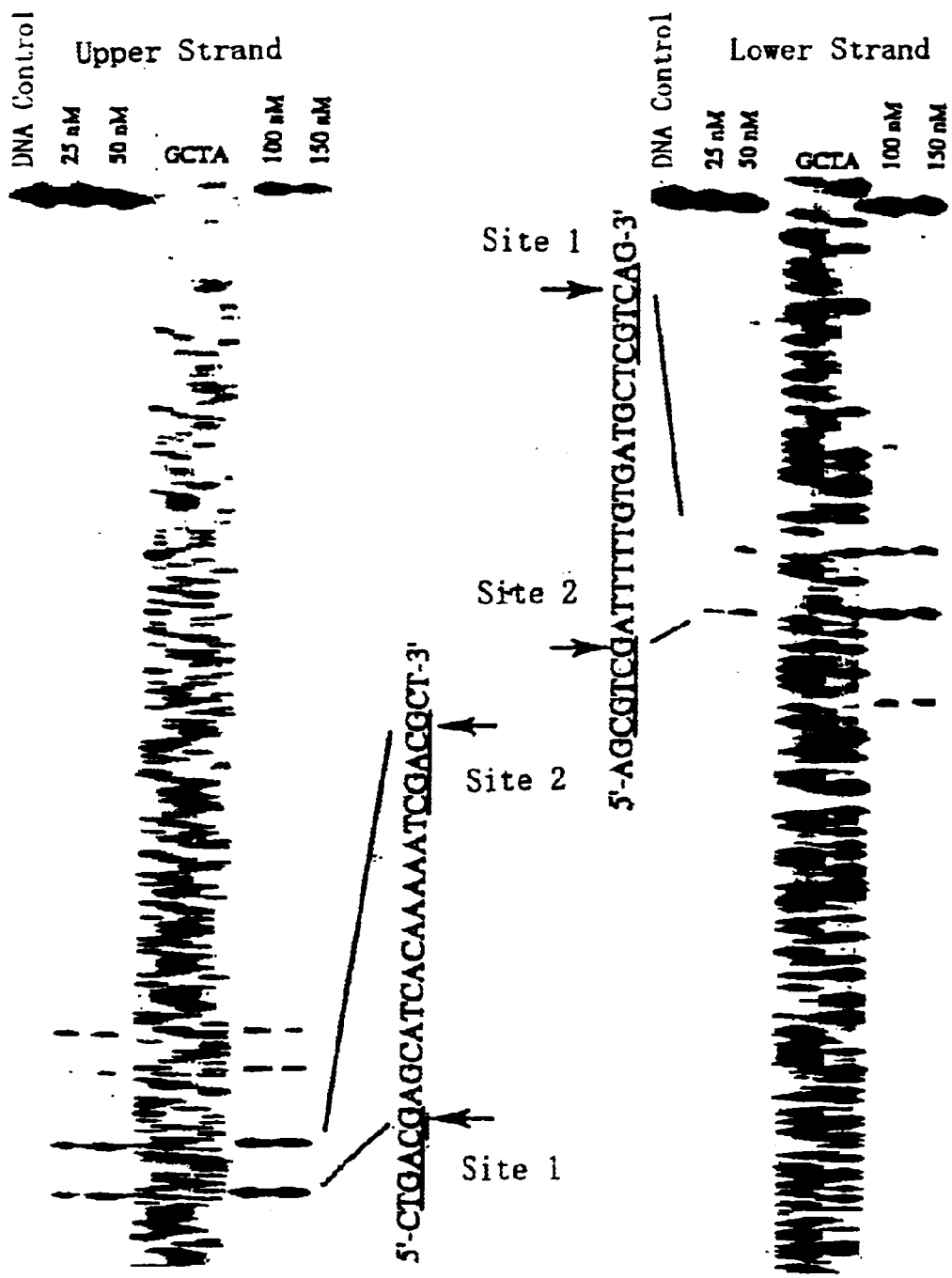
FIG. 1 is a drawing replaced by photograph showing result of a reaction with ImPyLDu86 of the present invention and DNA.

The present invention relates to a compound, which can simultaneously cleave double-strand of DNA, represented by the general formula (I)

$$B\text{—}L\text{—}A \qquad (I)$$

wherein B is a chemical structure which can recognize base sequence of DNA, A is a chemical structure which can bind with a base of DNA, and L is a linker which can link with a chemical structures of A and B.

Further, the present invention relates to a method for alkylating the specific part of base sequence of the double-strand DNA and a method for cleaving the specific part of base sequence of the double-strand DNA comprising using the compound hereinabove.

The present invention further relates to a pharmaceutical composition using these compounds, especially an anticancer agent.

A chemical structure moiety B, which can recognize base sequence of DNA, in the above general formula (I) of the present invention is preferably the chemical structure derived from optionally substituted pyrrole and/or imidazole. Substituents in pyrrole and imidazole are not limited, if these substituents do not inhibit to recognize base sequence of DNA. Examples of substituents are straight or branched alkyl having carbon atoms 1–10, preferably 1–5, alkoxy derived from the above alkyl, hydroxyl, amino, N-alkyl substituted amino derived from the above alkyl, N-acylamino derived from organic carboxylate, guanidino and substituted guanidino. Examples are N-methylpyrrole, N-methylimidazole, 3-hydroxypyrrole and N-methyl-3-hydroxypyrrole.

The chemical structural moiety B, which can recognize base sequence of DNA, is preferably, with more concretely, pyrrole-imidazole polyamide. Length (numbers) of pyrrole and imidazole are not limited, and are 2–10, preferably 2–5.

The chemical structural moiety A, which can bind with a base of DNA, is preferably the chemical structure having cyclopropane ring, and is more preferably alkylating moiety of duocarmycin.

The linker moiety L, which can link with chemical structures A and B, is preferably a chemical structure having an interval with proper distance between the segment A and the segment B, without losing alkylating activity. Preferable example is a chemical structure having vinyl group.

The compound of the present invention represented by the general formula (I) is preferably a compound represented by the following formula (hereinafter designates as "PyPyLDu86"):

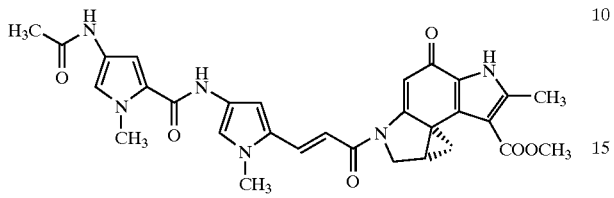

or a compound represented by the formula (hereinafter designates as "ImPyLDu86"):

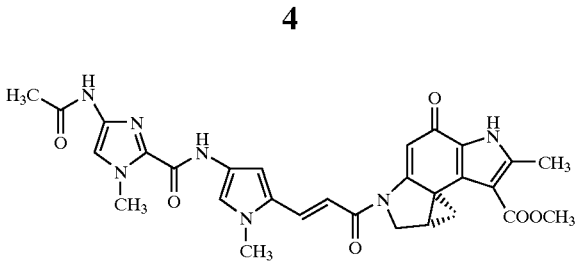

The above compounds recognize a base sequence TGACG or CGACG, or complementary strand thereof.

The compound represented by the general formula (I) of the present invention can be produced according to a known method. Namely, A-segment and B-segment are produced by the conventional method, and a linker segment L is bound with the above segment A or B, and the remaining segment is subsequently bound thereto.

Examples of production of the above ImPyLDu86 (7a) and PyPyLDu86 (7b) are shown in the following chemical reaction scheme. Numbers below each compound in the reaction scheme indicate compound No.

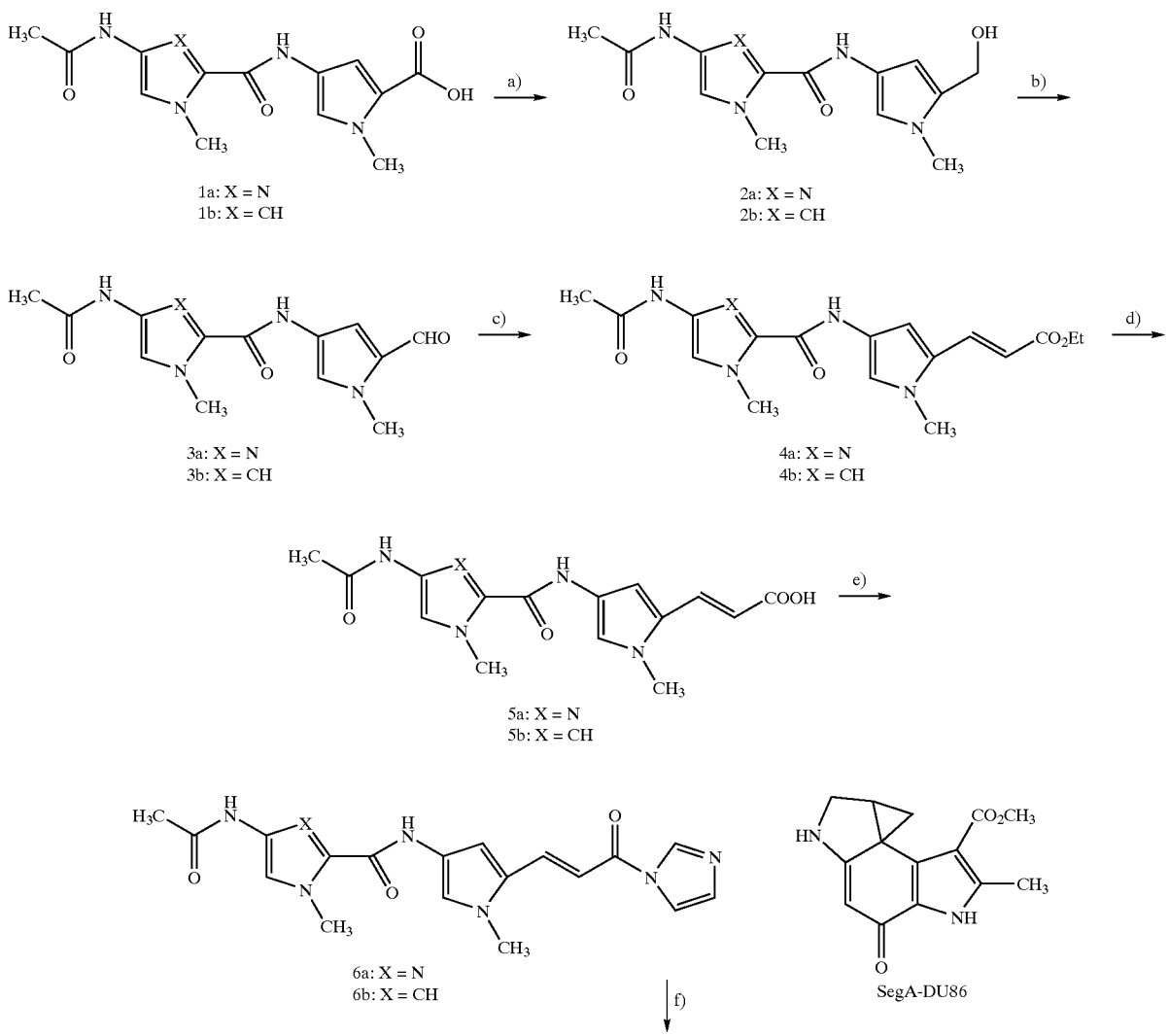

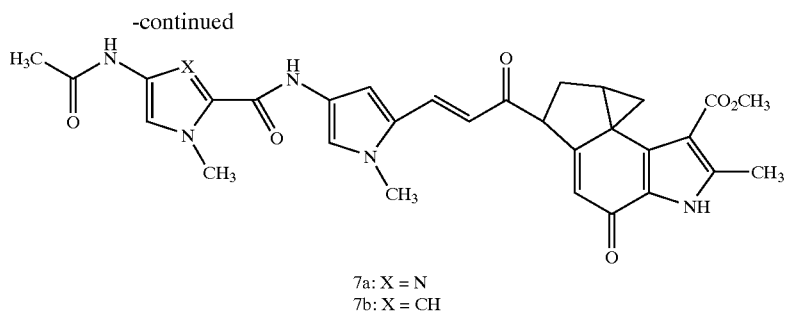

7a: X = N
7b: X = CH

Each reaction indicates as follows: a) a treatment with benzotriazole-1-yloxytris (dimethylamino) phosphonium hexafluorophosphate (BOP) and NaBH$_4$ in THF; b) a treatment with MnO$_2$ in THF; c) a treatment with triethyl phosphonoacetate and NaH in THF; d) a treatment with sodium hydroxide in water-methanol; e) a treatment with 1,1'-carbonyldiimidazole in DMF; and f) a treatment with segment A of DU86 using NaH in DMF.

Reactivities of the thus synthesized PyPyLDu86 and ImPyLDu86 with DNA were investigated. Result of alkylation using ImPyLDu86 is shown in FIG. 1. DNA used in this experiment and a structure of ImPyLDu86 used are shown in FIG. 2.

The left electrophoresis pattern is a result of the upper strand of the double-strand DNA, and the right electrophoresis pattern is a result of the lower strand of the double-strand DNA. Alkylating site can be observed by thermally induced strand cleavage. As a result, the double-strand DNA is mainly cleaved at the site 1 and the site 2 of the two strands from the lower concentration, and simultaneous alkylation on the two strands can be confirmed. No compounds have been known to occur such the cleavage, and in this sense, the compound of the present invention can be said as an artificial restriction enzyme. The efficiency of cleavage was found to approach high ratio of 70% calculated by an amount of used ImPyLDu86, and is unusually high efficiency as compared with that of the previously synthesized molecule (refer to Japanese Patent Application No. Hei 10-260710).

A reason for occurring simultaneous alkylation on the two strands may be, as shown in FIG. 3, that a dimerization of ImPyLDu86 recognizes GC base pair by constructing preferable stacking of the linker moiety and imidazole, and specifically binds with recognition sequence on the double-strand DNA. As the results, it was demonstrated that the linker, which was proposed and inserted by the molecular design, could increase the reactivity of the compound and could be applied as a recognition unit by pairing with imidazole. Based on these knowledge, we can say that we have taken a step toward the molecular design of the new type of drugs for gene therapy targeting on the specific sequence of DNA.

Cytotoxic activity of the compound of the present invention based on the properties described hereinbefore was examined. Cytotoxic activities of PyPyLDu86 and ImPyLDu86 of the present invention and known anticancer agent duocarmycin on HeLaS$_3$ cells (uterocervical squamous cell carcinoma cells) were tested. Results are shown in Table 1. the result indicates that the compounds of the present invention have approximately 3–7-fold activities as compared with duocarmycin.

The compound of the present invention is useful for anticancer agent and can be prepared as a pharmaceutical composition with addition of pharmaceutically acceptable carrier. The compound of the present invention can be administered orally or parenterally depending on symptoms. Effective dose of the pharmaceutical composition of the present invention can be selected, although depending on conditions and symptoms of patients, generally within a range of 1 μg–100 mg/kg/day. The pharmaceutical composition of the present invention can be formulated by conventional method for the preparation for injection.

EXAMPLES

Following examples illustrate the present invention more concretely, but the present invention is not construed as limiting within these examples.

Abbreviations of reagents used in the following examples are as follows.

DIEA: N,N-diisopropylethylamine,
DMF: N,N-dimethylformamide,
THF: tetrahydrofuran and
BOP: benzotriazole-1-yloxytris (dimethylamino)-phosphonium hexafluorophosphate.

In the following examples, reactions were monitored by thin-layer chromatography (TLC) using 0.25 mm silica gel 60 plates impregnated with 254 nm fluorescent indicator (Merck). TLC plates were visualized by UV light.

In NMR spectra, tetramethylsilane was used as the internal standard, and chemical shifts of H1-NMR spectra were recorded in ppm.

EI (Electron impact) mass spectra were recorded on a JNM-AX 505, and ESIMS (Electrospray ionization mass spectra) was recorded on a PE SCIEX API 165. Ex Taq DNA polymerase and filter tube (Suprec-02) were purchased from Takara Shuzo Co., thermo sequenase core sequencing kit and loading dye (dimethylformamide with fushin red) from Amersham Co., 5'-end Texas Red-modified DNA oligomer (18 mer) from Kurabo Co., and 50% Long Ranger gel solution from FMC Bioproducts. Polyacrylamide gel electrophoresis was performed on a HITACHI 5500-S DNA sequencer.

Example 1

Production of Compound 2a (X=N)

NaBH$_4$ 98 mg (2.59 mmol) was added to a solution of 204.8 mg (0.67 mmol) of compound 1a, BOP 326.3 mg (0.74 mmol) and DIEA 170 μl in THF 30 ml. The reaction mixture was stirred for 3 hours at room temperature and solvent was distilled off in vacuo to give a residue, to which CH$_3$OH 20 ml and water 5 ml were added. The solution was stirred for 1 hour to obtain a clear solution. The solvents were removed in vacuo, and the resultant yellow residue was purified by flash chromatography using CH$_3$OH and CH$_2$Cl$_2$ to obtain the objective compound 2a 92.6 mg yield 47.4%.

¹H NMR (DMSO-d₆) δ 10.24 (s, 1H), 9.62 (s, 1H), 7.38 (s, 1H), 7.10 (d, J=2.0 Hz, 1H), 6.09 (d, J=2.0 Hz, 1H), 4.86 (t, J=5.5 Hz, 1H), 4.34 (d, J=5.5 Hz, 2H), 3.93 (s, 3H), 3.54 (s, 3H), 2.01 (s, 3H).

Example 2

Production of Compound 2b (X=CH)

Compound 2b was obtained in yield 68.5% in a similar manner as the compound 2a.

¹H NMR (DMSO-d₆) δ 9.76 (s, 1H), 9.64 (s, 1H), 7.10 (d, J=2.0 Hz, 1H), 7.05 (d, J=2.0 Hz, 1H), 6.78 (d, J=2.0 Hz, 1H), 6.01 (d, J=2.0 Hz, 1H), 4.82 (t, J=5.5 Hz, 1H), 4.34 (d, J=5.5 Hz, 2H), 3.80 (s, 3H), 3.53 (s, 3H), 1.96 (s, 3H).

Example 3

Production of Compound 3a (X=N)

A mixture of 85 mg (0.29 mmol) of compound 2a and activated MnO₂ (85%) 550 mg was added in THF 30 ml, and the mixture was stirred at room temperature for 1.5 hour and filtered. The residue obtained by removal of solvent in vacuo was analyzed by ¹H NMR to confirm that the residue had sufficient purity for use in the next reaction step without further purification.

¹H NMR (DMSO-d₆) δ 10.21 (s, 1H), 10.18 (s, 1H), 9.50 (s, 1H), 7.63 (s, 1H), 7.43 (s, 1H), 7.10 (d, J=2.0 Hz, 1H), 3.94 (s, 3H), 2.84 (s, 3H), 2.02 (s, 3H).

Example 4

Production of Compound 3b (X=CH)

Compound 3b was obtained in yield 68.5% in a similar manner as the compound 3a.

¹H NMR (DMSO-d₆) δ 9.99 (s, 1H), 9.80 (s, 1H), 9.49 (s, 1H), 7.57 (s, 1H), 7.14 (d, J=1.0 Hz, 1H), 6.98 (d, J=1.0 Hz, 1H), 6.88 (d, J=2.0 Hz, 1H), 3.87 (s, 3H), 3.82 (s, 3H), 1.97 (s, 3H).

Example 5

Production of compound 4a (X=N)

NaH (60%) 23.1 mg (0.58 mmol) was dissolved in THF 6 ml, and triethyl phosphonoacetate 116 ml was added thereto under ice cooling. The reaction mixture was stirred for 5 minutes, and a solution of compound 3a dissolved in THF 25 ml was added thereto. The resulting mixture was stirred for overnight. THF was distilled off in vacuo. The obtained residue was subjected to flash chromatography using ethyl acetate. Compound 4a was obtained as yellow solid 88.5 mg in yield 84% (yield of two steps based on 2a).

¹H NMR (DMSO-d₆) δ 10.25 (s, 1H), 9.87 (s, 1H), 7.51 (d, J=15.9 Hz, 1H), 7.44 (d, J=1.8 Hz, 1H), 7.42 (s, 1H), 6.84 (d, J=1.8 Hz, 1H), 6.11 (d, J=15.9 Hz, 1H), 4.16 (q, J=7.0 Hz, 2H), 4.13 (s, 3H), 3.70 (s, 3H), 2.02 (s, 3H), 1.24 (t, J=7.0 Hz, 3H).

Example 6

Production of Compound 4b (X=CH)

Compound 4b was obtained in yield 55% in a similar manner as the compound 4a.

¹H NMR (DMSO-d₆) δ 9.87 (s, 1H), 9.78 (s, 1H), 7.51 (d, J=15.5 Hz, 1H), 7.39 (d, J=2.0 Hz, 1H), 7.13 (d, J=2.0 Hz, 1H), 6.85 (d, J=2.0 Hz, 1H), 6.73 (d, J=2.0 Hz, 1H), 6.07 (d, J=15.5 Hz, 1H), 4.16 (q, J=7.0 Hz, 2H), 3.82 (s, 3H), 3.68 (s, 3H), 1.97 (s, 3H), 1.23 (t, J=7.0 Hz, 3H).

Example 7

Production of Compound 5a (X=N)

2N dil. NaOH 1.5 ml and water 3 ml were added to a solution of 70 mg (0.2 mmol) of compound 4a in CH₃OH 5 ml. The mixture was stirred at room temperature for 4.5 hours.

After removal of solvent by vacuum distillation, water 20 ml was added to the residue. The resulting solution was filtered, and the filtrate was acidified with 2N HCl to pH 2–3. The thus obtained gel-like precipitate was collected by filtration and dried to obtain 43 mg of compound 5a in yield 67%.

¹H NMR (DMSO-d₆) δ 10.24 (s, 1H), 9.84 (s, 1H), 7.43 (d, J=15.0 Hz, 1H), 7.41 (s, 1H), 7.40 (s, 1H), 6.78 (s, 1H), 6.03 (d, J=15.0 Hz, 1H), 3.94 (s, 3H), 3.67 (s, 3H), 3.86 (s, 3H);

ESIMS m/e

| As $C_{15}H_{16}N_5O_4$; | Calculated value (M-H) | 330.3 |
|---|---|---|
| | Observed value | 330.2 |

Example 8

Production of Compound 5b (X=CH)

Compound 5b was obtained in yield 57% in a similar manner as the compound 5a.

¹H NMR (DMSO-d₆) δ 9.83 (s, 1H), 9.78 (s, 1H), 7.38 (d, J=16.0 Hz, 1H), 7.34 (s, 1H), 7.13 (d, J=2.0 Hz, 1H), 6.84 (d, J=2.0 Hz, 1H), 6.64 (s, 1H), 5.99 (d, J=16.0 Hz, 1H), 3.82 (s, 3H), 3.65 (s, 3H), 1.99 (s, 3H);

ESIMS m/e

| As $C_{16}H_{17}N_4O_4$; | Calculated value (M-H) | 329.3 |
|---|---|---|
| | Observed value | 329.4 |

Example 9

Production of Compound 6a (X=N)

1,1'-carboxyldiimidazole 49.9 mg (0.31 mmol) was added to a solution of 26.4 mg (0.08 mmol) of compound 5a in DMF 2 ml. The reaction mixture was stirred overnight at room temperature, and water 20 ml was added. The mixture was filtered to obtain 20.5 mg of compound 6a as yellow precipitate in yield 68%.

¹H NMR (DMSO-d₆) δ 10.23 (s, 1H), 10.04 (s, 1H), 8.67 (s, 1H), 7.90 (d, J=1.0 Hz, 1H), 7.88 (d, J=15.5 Hz, 1H), 7.50 (d, J=2.0 Hz, 1H), 7.44 (s, 1H), 7.32 (d, J=2.0 Hz, 1H), 7.16 (d, J=15.5 Hz, 1H), 7.10 (s, 1H), 3.96 (s, 3H), 3.79 (s, 3H), 2.03 (s, 3H);

ESIMS m/e

| As C₁₈H₁₈N₇O₃; | Calculated value (M-H) | 380.4 |
|---|---|---|
| | Observed value | 380.4 |

Example 10

Production of Compound 6b (X=CH)

Compound 6b was obtained in yield 80% in a similar manner as the compound 6a.

$^1$H NMR (DMSO-d$_6$) δ 10.1 (s, 1H), 9.82 (s, 1H), 8.68 (s, 1H), 7.91 (t, J=2.0 and 2.0 Hz, 1H), 7.87 (d, J=15.0 Hz, 1H), 7.48 (d, J=2.0 Hz, 1H), 7.22 (d, J=2.0 Hz, 1H), 7.16 (d, J=1.5 Hz, 1H), 7.14 (d, J=15.0 Hz, 1H), 7.10 (s, 1H), 6.89 (d, J=1.5 Hz, 1H), 3.84 (s, 3H), 3.78 (s, 3H), 1.97 (s, 3H);

ESIMS m/e

| As C₁₉H₁₉N₆O₃; | Calculated value (M-H) | 379.4 |
|---|---|---|
| | Observed value | 379.4 |

Example 11

Production of Compound 7a (X=N)

A solution of 6.1 mg (0.024 mmol) of segment A of DU86 dissolved in DMF 0.3 ml was added to a solution of sodium hydride (60%) 3.2 mg (0.08 mmol) dissolved in DMF 0.3 ml at −50° C. The mixture was stirred at −50 to −40° C. for 3 hours. After a solution of 10.8 mg (0.028 mmol) of compound 6a dissolved in DMF 1 ml was added at −50° C., the reaction mixture was further stirred at −40° C. for 5 hours, and allowed to stand at −30° C. in a refrigerator for 2 days. Then sodium phosphate buffer (0.01 M) 3 ml was added, and the mixture was stirred at room temperature for 5 minutes. The yellow residue obtained by distilled off the solvent in vacuo was purified by flash chromatography using CH$_3$OH and CHCl$_3$ to obtain 12.3 mg of compound 7a in yield 91%.

$^1$H NMR (DMSO-d$_6$) δ 12.36 (s, 1H), 10.24 (s, 1H), 9.97 (s, 1H), 7.58 (d, J=15.0 Hz, 1H), 7.43 (s, 1H), 7.41 (d, J=2.0 Hz, 1H), 6.99 (d, J=2.0 Hz, 1H), 6.85 (s, 1H), 6.58 (d, J=15.0 Hz, 1H), 4.29 (d, J=10.5 Hz, 1H), 4.19 (dd, J=5.0 Hz and 4.5 Hz, 1H), 3.95 (s, 3H), 3.73 (s, 3H), 3.72 (s, 3H), 3.46 (m, 1H), 2.47 (s, 3H), 2.08 (m, 1H), 2.02 (s, 3H), 1.29 (t, J=4.5 and 3.5 Hz, 1H);

ESIMS m/e

| As C₂₉H₂₈N₇O₆; | Calculated value (M-H) | 570.6 |
|---|---|---|
| | Observed value | 570.4 |

Example 12

Production of Compound 7b (X=CH)

Compound 7b was obtain in yield 77% in a similar manner as the compound 7a.

$^1$H NMR (DMSO-d$_6$) δ 12.36 (s, 1H), 9.90 (s, 1H), 9.80 (s, 1H), 7.57 (d, J=15.0 Hz, 1H), 7.38 (d, 1.5 Hz, 1H), 7.14 (d, J=2.0 Hz, 1H), 6.88 (d, 1.5 Hz, 1H), 6.86 (d, J=2.0 Hz, 1H), 6.84 (s, 1H), 6.56 (d, J=15.0 Hz, 1H), 4.29 (d, J=10.5 Hz, 1H), 4.19 (dd, J=4.0 and 4.5 Hz, 1H), 3.83 (s, 3H), 3.73 (s, 1H), 3.71 (s, 1H), 3.46 (m, 1H), 2.47 (s, 3H), 2.09 (m, 1H), 1.97 (s, 3H), 1.29 (t, J=4.5 and 3.5 Hz, 1H);

ESIMS m/e

| As C₃₀H₂₉N₆O₆; | Calculated value (M-H) | 569.6 |
|---|---|---|
| | Observed value | 569.5 |

Example 13

Alkylation of 450 bp DNA Fragments (1) Preparation of 5'-texas red-end-modified 450 bp DNA fragment The 5'-end texas red-modified 450 bp DNA fragments pUC18 F780*-1229 and pUC18 R1459*-1908 (these are complementary) were prepared by the PCR method using 5'-end texas red-modified 18mers as primers and purified by filtration using Suprec-02. The concentration was determined by ethidium bromide staining. The asterisk (*) indicates texas red modification site, and numerals indicates nucleotide numbering from the replication origin.

(2) High-resolution gel electrophoresis

A standard reaction mixture containing 5'-end texas red-labeled DNA fragment 60 nM, DMF 5% (v/v) and various concentrations of drugs in total 10 μl of sodium phosphate buffer (pH 7.0) 12.5 mM was added into microcentrifugal tube (Eppendorf tube) and allowed to stand at room temperature for overnight. Calf thymus DNA (5 mM, 1 μl) was added thereto and heated at 90° C. for 5 minutes. DNA was collected by ethanol precipitation. The thus obtained DNA was dissolved in loading dye (DMF solution of fushin red) 8 μl. The sample solution was heated at 94° C. for 20 minutes for denaturation of DNA, and immediately cooled to 0° C. A 2 μl of aliquot was electrophoresed on polyacrylamide gel using 6% Long Ranger (trademark) gel solution using 5500-S DNA sequencer system.

Example 14

Growth Inhibitory Test on HeLaS$_3$ Cells

Suspension 0.75 ml of HeLaS$_3$ cells, 2.67×10$^4$ cells/ml, in MEM medium containing 10% fetal bovine serum and 2 mM glutamine, was dispensed into each well in 24 cell culture plate. After incubation in the CO$_2$-incubator at 37° C. for overnight, 0.25 ml portions of each test compound shown in Table 1, which was appropriately diluted with medium, was added into each well.

After cells were incubated for 72 hours in the CO$_2$-incubator, the culture supernatant was removed, and cells were dispersed using trypsin-ethylenediaminetetraacetic acid (EDTA) and collected. Cell counts were counted by cell counter, and cell counts without treatment and cell counts treated with known concentration of test compound were compared to calculate the concentration of test compound which inhibits 50% of cell growth (IC$_{50}$). Results are shown in the following table.

| Test Compound | IC$_{50}$ (nM) |
|---|---|
| PyPyLDu86 | 1.5 |
| ImPyLDu86 | 0.7 |
| Duocaraycin | 4.7 |

Industrial Applicability

The present invention provides chemically synthesized compound, which can simultaneously alkylating or cleaving double-strand DNA. The compound is not only useful for artificial restriction enzyme but also useful for gene therapy targeting the specific base sequence.

What is claimed is:

1. A compound which simultaneously alkylates and cleaves double-stranded deoxyribonucleic acid (DNA), wherein the compound is represented by the following formula

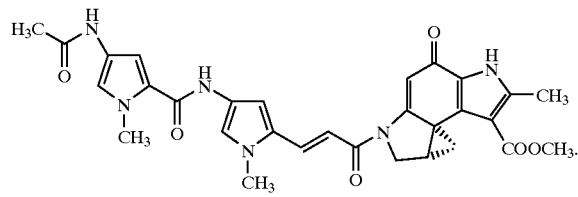

2. A composition comprising the compound of claim 1 and a pharmaceutically acceptable carrier.

3. The composition according to claim 2 wherein the compound is present in an amount effective to inhibit growth of tumor cells.

4. A compound which simultaneously alkylates and cleaves double-stranded deoxyribonucleic acid (DNA), wherein the compound is represented by the following formula

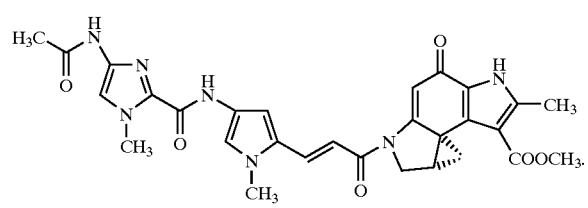

5. A composition comprising the compound of claim 4 and a pharmaceutically acceptable carrier.

6. The composition according to claim 5 wherein the compound is present in an amount effective to inhibit growth of tumor cells.

* * * * *

SEQUENCE LISTING

<160> NUMBER OF SEQ ID NOS: 3

<210> SEQ ID NO 1
<211> LENGTH: 450
<212> TYPE: DNA
<213> ORGANISM: Artificial Sequence
<220> FEATURE:
<223> OTHER INFORMATION: Description of Artificial Sequence: Synthetic pUC 18

<400> SEQUENCE: 1

```
agaatcaggg gataacgcag gaaagaacat gtgagcaaaa ggccagcaaa aggccaggaa      60
ccgtaaaaag gccgcgttgc tggcgttttt ccataggctc cgcccccctg acgagcatca     120
caaaaatcga cgctcaagtc agaggtggcg aaacccgaca ggactataaa gataccaggc     180
gtttccccct ggaagctccc tcgtgcgctc tcctgttccg accctgccgc ttaccggata     240
cctgtccgcc tttctccctt cgggaagcgt ggcgctttct caatgctcac gctgtaggta     300
tctcagttcg gtgtaggtcg ttcgctccaa gctgggctgt gtgcacgaac cccccgttca     360
gcccgaccgc tgcgccttat ccgtaacta tcgtcttgag tccaacccgg taagacacga     420
cttatcgcca ctggcagcag ccactggtaa                                     450
```

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2

```
ctgacgagca tcacaaaaat cgacgct                                          27
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3

```
agcgtcgatt tttgtgatgc tcgtcag                                          27
```